US012342652B2

(12) United States Patent
Liu et al.

(10) Patent No.: US 12,342,652 B2
(45) Date of Patent: Jun. 24, 2025

(54) DETECTION DEVICE

(71) Applicant: Lextar Electronics Corporation, Hsinchu (TW)

(72) Inventors: Ke-Wei Liu, Hsinchu (TW); Yen-Chih Chou, Hsinchu (TW); Ming-Jing Lee, Hsinchu (TW)

(73) Assignee: Lextar Electronics Corporation, Hsinchu (TW)

( * ) Notice: Subject to any disclaimer, the term of this patent is extended or adjusted under 35 U.S.C. 154(b) by 492 days.

(21) Appl. No.: 17/654,595

(22) Filed: Mar. 14, 2022

(65) Prior Publication Data

US 2023/0011488 A1 Jan. 12, 2023

(30) Foreign Application Priority Data

Jul. 7, 2021 (TW) .................................. 110124892

(51) Int. Cl.
*H10F 77/00* (2025.01)
*H10F 55/255* (2025.01)
*H10F 77/40* (2025.01)
*H10F 77/50* (2025.01)
*A61B 5/00* (2006.01)
*A61B 5/1455* (2006.01)

(52) U.S. Cl.
CPC ......... *H10F 55/255* (2025.01); *H10F 77/407* (2025.01); *H10F 77/50* (2025.01); *H10F 77/933* (2025.01); *A61B 5/14552* (2013.01); *A61B 5/681* (2013.01)

(58) Field of Classification Search
CPC ................. H01L 31/02; H01L 31/0203; H01L 31/02005; H01L 31/0232; H01L 31/02325; H01L 31/173; H10F 55/255; H10F 77/00; H10F 77/40; H10F 77/50; H10F 77/407; H10F 77/933; A61B 5/00; A61B 5/024; A61B 5/1455; A61B 5/681; A61B 5/14552; A61B 5/02444; A61B 5/02438
USPC .......................................................... 257/82
See application file for complete search history.

(56) References Cited

U.S. PATENT DOCUMENTS

| 10,401,296 | B1 | 9/2019 | Muller et al. |
| 2003/0030002 | A1 | 2/2003 | Safai |
| 2009/0159776 | A1 | 6/2009 | Maeda et al. |
| 2016/0242646 | A1 | 8/2016 | Obma |
| 2020/0107435 | A1 | 4/2020 | He et al. |
| 2020/0107436 | A1 | 4/2020 | He et al. |

FOREIGN PATENT DOCUMENTS

| CN | 101621956 A | 1/2010 |
| CN | 103531583 A | 1/2014 |
| CN | 104586370 A | 5/2015 |
| CN | 111134591 A | 5/2020 |

(Continued)

*Primary Examiner* — Chuong A Luu
(74) *Attorney, Agent, or Firm* — CKC & Partners Co., LLC

(57) ABSTRACT

A detection device includes a substrate, a light-emitter, and a light receiver. The substrate includes a first surface area and a second surface area, in which the first surface area has a first reflectance greater than a second reflectance of the second surface area. The light emitter is disposed on the first surface area, and the light receiver is disposed on the second surface area. The light receiver has a third reflectance which is substantially the same as the second reflectance of the second surface area.

10 Claims, 6 Drawing Sheets

(56) References Cited

FOREIGN PATENT DOCUMENTS

| | | | |
|---|---|---|---|
| CN | 111214209 | A | 6/2020 |
| CN | 111436917 | A | 7/2020 |
| EP | 4 239 240 | A1 * | 10/2021 |
| JP | 2015221177 | A | 12/2015 |
| TW | 200505063 | A | 2/2005 |
| TW | 201640091 | A | 11/2016 |
| TW | 202014979 | A | 4/2020 |
| TW | 202021150 | A | 6/2020 |
| TW | I698125 | B | 7/2020 |
| TW | I698613 | B | 7/2020 |
| TW | 202109032 | A | 3/2021 |

* cited by examiner

DETECTION DEVICE

CROSS-REFERENCE TO RELATED APPLICATION

This application claims priority to Taiwan Application Serial Number 110124892, filed Jul. 7, 2021, which is herein incorporated by reference in its entirety.

BACKGROUND

Field of Invention

The present invention relates to a detection device. More particularly, the present invention relates to a detection device applied to human bodies.

Description of Related Art

The medical testing technology has already progressed from invasive testing to non-invasive testing due to the advancement of science and technology.

In the process of detection, optical principles are used to detect a human body by some detection devices, and consumers always take the convenience of the optical detection devices in account. If the optical detection device is too large, it is unfavorable for the user to carry or wear. In addition, the manufacturers would like to show users new experience which is different from the existing optical detection devices, so as to attract more customers.

Therefore, how manufacturers can provide an optical detection device that can be miniaturized and innovative concepts for enhancing the convenience of use and product competitiveness has become one of the important issues.

SUMMARY

The invention provides a detection device which includes a substrate, a light-emitter, and a light receiver. The substrate includes a first surface area and a second surface area, in which the first surface area has a first reflectance greater than a second reflectance of the second surface area. The light emitter is located on the first surface area. The light receiver is located on the second surface area, and the light receiver has a third reflectance which is substantially the same as the second reflectance of the second surface area.

In some embodiments of the present invention, the light receiver has a color the same as a color of the second surface area.

In some embodiments of the present invention, the second surface area surrounds a periphery of the first surface area.

In some embodiments of the present invention, the first surface area is circular, and the second surface area is annular.

In some embodiments of the present invention, the detection device including a first wall disposed between the first surface area and the second surface area.

In some embodiments of the present invention, the detection device includes a second wall extending along a periphery of the second surface area.

In some embodiments of the present invention, the first wall includes a surface facing toward the light emitter and having the first reflectance, and the first wall includes another surface facing toward the light receiver and having the second reflectance.

In some embodiments of the present invention, the first reflectance is greater than or equal to 90%, and the second reflectance is smaller than or equal to 10%.

In some embodiments of the present invention, the detection device further includes an optical top cap which has an optical lens and a third wall, and the optical lens has an inner surface and an outer surface. The third wall is disposed on the inner surface of the optical lens, and the third wall is in contact with the first wall to form a space accommodating the light receiver.

In some embodiments of the present invention, the detection device further includes a second wall extending along a periphery of the second surface area and a fourth wall disposed on the inner surface, and the fourth wall is in contact with the second wall to form a space accommodating the light receiver.

In some embodiments of the present invention, the light emitter is electrically connected to the substrate in a flip chip package or in a wire bonding package.

In some embodiments of the present invention, the light receiver is electrically connected to the substrate in a flip chip package or in a wire bonding package.

In embodiments of the present invention, a detection device is provided, and the detection device includes a substrate, a light emitter, and a light receiver. The light emitter with high reflectance is located on an area, and the light receiver with low reflectance is located on another area. Therefore, it is benefit for the light emitter to efficiently generate detection light outward, and stray light around the light receiver is absorbed, so as to prevent the stray light from affecting the light receiver.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
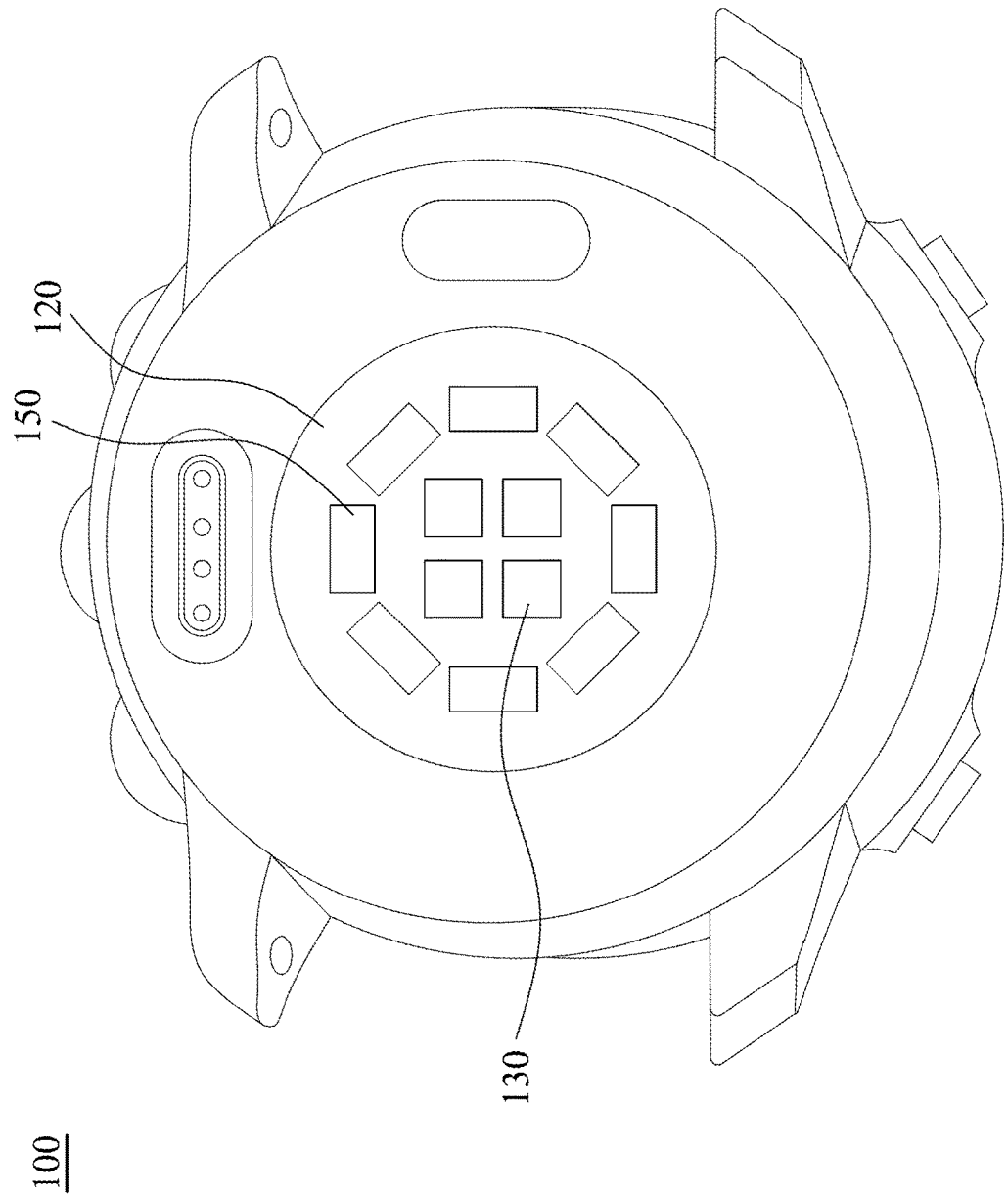
FIG. 1 illustrates a schematic view of a detection device in accordance with some embodiments of the present invention.

Reference will now be made in detail to the present embodiments of the invention, examples of which are illustrated in the accompanying drawings. Wherever possible, the same reference numbers are used in the drawings and the description to refer to the same or like parts.

Reference is made to FIG. 1, which illustrates a schematic view of a detection device. In some embodiments of the present invention, the detection device 100 includes a smart watch which is able to detect blood oxygen and pulse. The present invention is not limited in this respect. The detection device 100 includes an optical top cap 120, a light emitter 130, and a light receiver 150, and the light emitter 130 can generate detection light to human body through the optical top cap 120. Therefore, the detection light can be reflected by the human body and received by the light receiver 150, so as to complete light detection to the human body.

In some embodiments of the present invention, the light emitter 130 can include a light-emitting diode (LED), such as organic LED (OLED), mini LED, and micro LED. The present invention is not limited in this respect. In some embodiments of the present invention, the light receiver 150 is disposed with respect to light frequency of the light emitter 130. If the light emitter 130 includes a red light resource and/or an infrared light resource, the light receiver 150 includes red light sensor and/or infrared light sensor. In addition, if the light emitter 130 includes a green light source, the light receiver 150 includes a green light sensor for detecting the pulse rate of human bodies.

Figure 2:
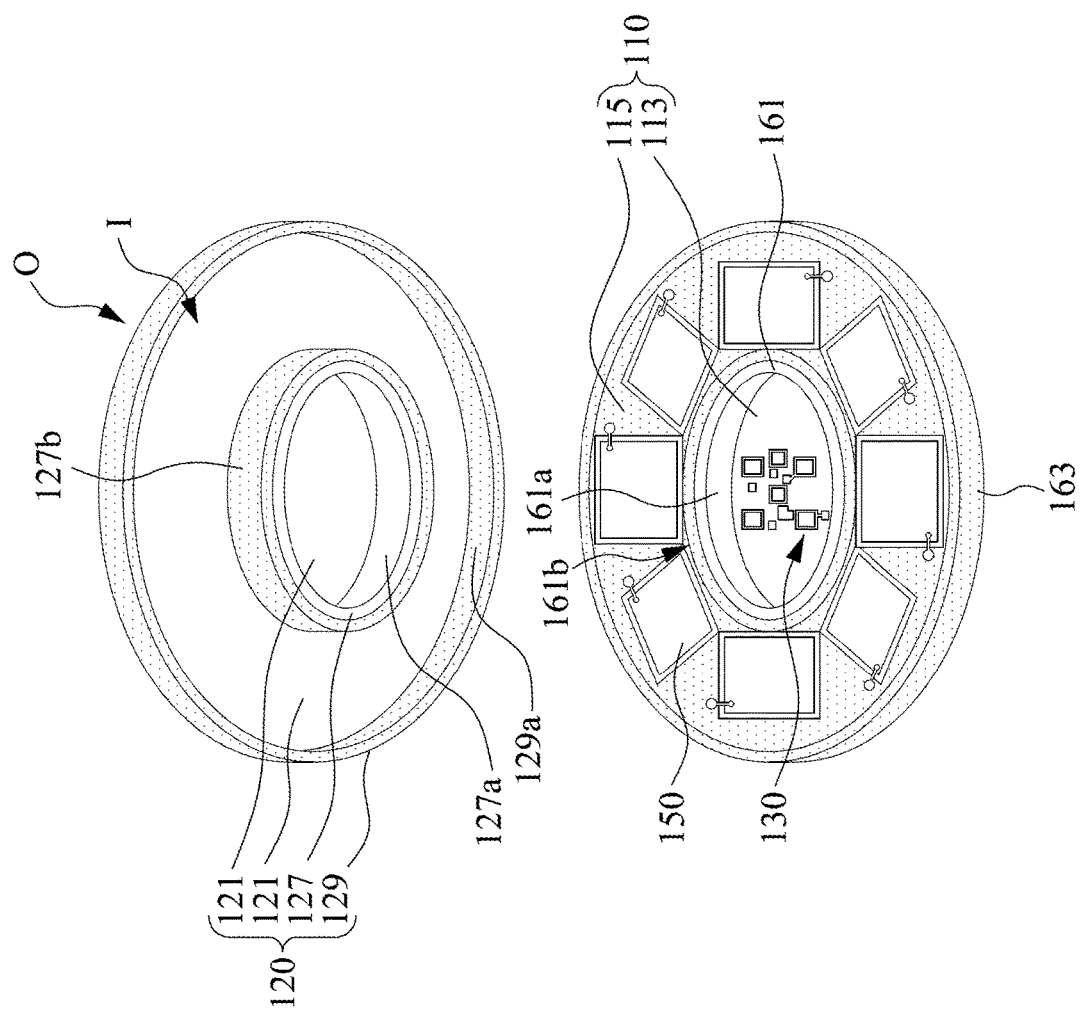
FIG. 2 illustrates an internal view of the detection device in FIG. 1.
Figure 3:
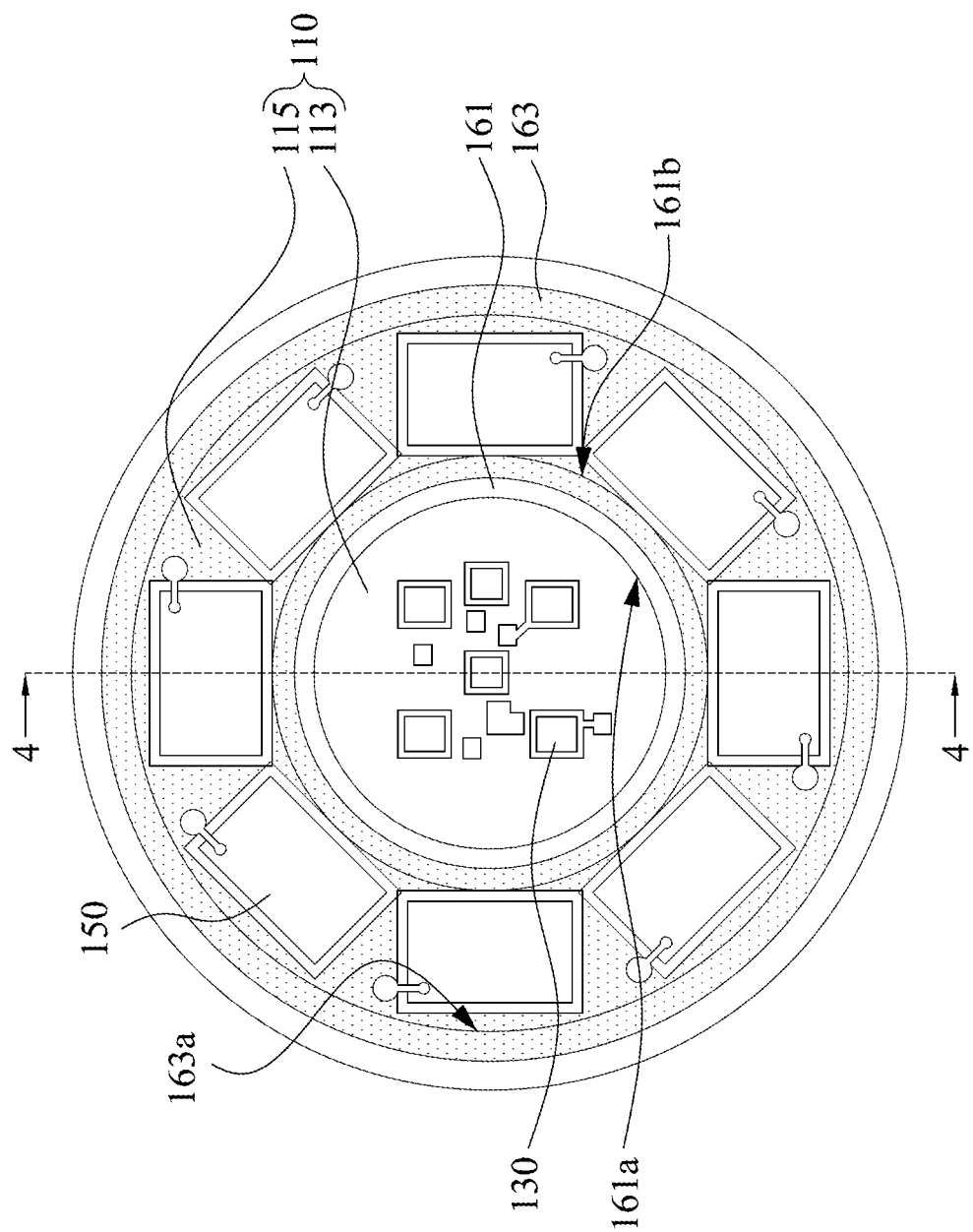
FIG. 3 illustrates an internal view of the detection device in FIG. 1 according to a view point different from FIG. 2.
Figure 4:
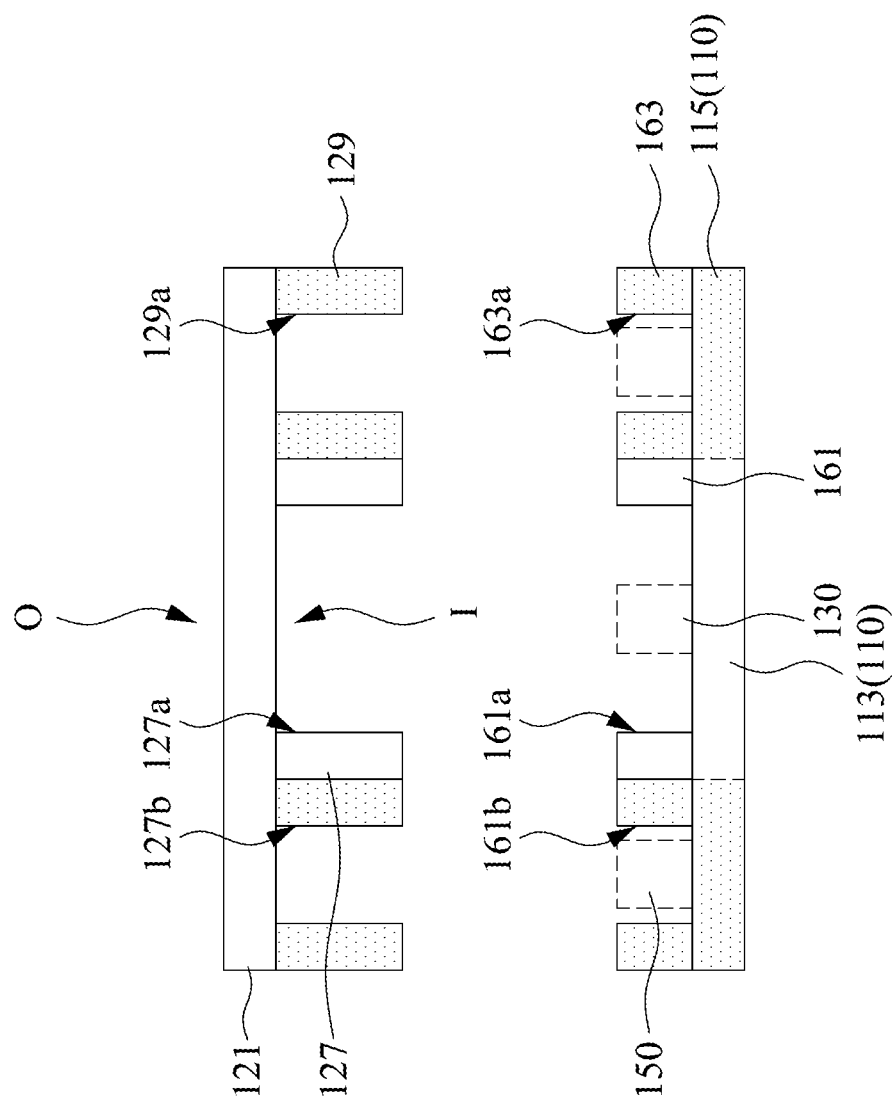
FIG. 4 illustrates a cross section view taken from the line 4-4 in FIG. 3.

Reference is made to FIGS. 2-4. FIG. 2 illustrates an internal view of the detection device 100 in FIG. 1. FIG. 3 illustrates an internal view of the detection device 100, in which FIGS. 2 and 3 respectively show different viewpoints. FIG. 4 illustrates a cross section view of the detection device 100 taken from line 4-4 in FIG. 3. In some embodiments of the present invention, the detection device 100 includes a substrate 110 which can be disposed inside the detection device 100. The substrate 110 includes a first surface area 113 and a second surface area 115, in which the first surface area 113 has a first reflectance greater than a second reflectance of the second surface area 115. In addition, the light emitter 130 is located on the first surface area 113, and the light receiver 150 is located on the second surface area 115. The light receiver 150 has a reflectance the same as the second reflectance of the second surface area 115, and thus the light receiver 150 has an appearance reflectance the same as the second reflectance of the second surface area 115. The present invention is not limited in this respect. Since both the second surface area 115 and the light receiver 150 have low reflectance for absorbing stray light around the light receiver, the light receiver 150 has an outstanding light receiving ability.

In some embodiments of the present invention, the substrate 110 can include a rigid substrate, a flexible substrate, a glass substrate, a sapphire substrate, a silicon substrate, a printed circuit board, a metal substrate, or a ceramic substrate, and the present invention is not limited in this respect.

In some embodiments of the present invention, the light receiver 150 has an appearance color the same as a color of the second surface area 115, and both the second surface area 115 and the light receiver 150 can be black, purple, or blue for absorbing the stray light and preventing the stray light from affecting the light receiver 150. Moreover, the first surface area 113 and the second surface area 115 can be painted by solder mask coating, and the first surface area 113 and the second surface area 115 respectively have the first reflectance and the second reflectance which is different from the first reflectance. The color of the first surface area 113 or the color of the second surface area 115 can be original color of the substrate 110. For instance, if the substrate 110 is purple, the solder mask coating can be applied to the first surface area 113, such that the first surface area 113 has a white surface. The second surface area 115 has the purple surface of the substrate 110, and the first surface area 113 has the first reflectance greater than the second reflectance of the second surface area 115. In addition, the first surface area 113 and the second surface area 115 have opaque materials for blocking light, and the opaque materials can include a light-absorbing material or a reflective material.

Specifically, light-absorbing materials have dark color which is hard to reflect light, and the light-absorbing material includes bismaleimide triazine resin and a light blocking material, such as black ink, metal, resin, and/or graphite. The metal can include chromium or nickel. In addition, the resin, such as polyimide and acrylate, can be used to form a main body, and the light-absorbing material, such as carbon and titanium oxide ($Ti_3O_5$ or $Ti_4O_7$), can be evenly added to the main body. The light-absorbing material can be a mixture which includes a base and a light-absorbing substance. The base can be formed from a silicone-based material or an epoxy-based material, and the light-absorbing substance can include carbon, titanium oxide, or dark pigment. The present invention is not limited in this respect.

The reflective material is a mixture which includes a base and a high reflective substance, and the base is formed from a silicone-based material or an epoxy-based material. The high reflective substance can include titanium dioxide ($TiO_2$), silicon dioxide ($SiO_2$), aluminum oxide ($Al_2O_3$), potassium titanium oxide ($K_2TiO_3$), zirconium dioxide ($ZrO_2$), zinc sulfide (ZnS), zinc oxide (ZnO), or magnesium oxide (MgO).

In some embodiments of the present invention, the first reflectance is equal to or greater than 90%, and the second reflectance is equal to or smaller than 10%. In some preferable embodiments, the first reflectance is equal to or greater than 95%, and the second reflectance is equal to or smaller than 5%. In the most preferable embodiments, the first reflectance is equal to or greater than 99%, and the second reflectance is equal to or smaller than 1%. The higher first reflectance can improve the illuminating efficiency of the light emitter 130, and the lower second reflectance is benefit for improving light receiving ability of the light receiver 150, so as to prevent the stray light from affecting the light receiver 150.

In some embodiments of the present invention, the second surface area 115 surrounds a periphery of the first surface area 113. The first surface area 113 is circular, and the second surface area 115 is annular. In addition, the detection device 100 includes a plurality of the light emitters 130 and a plurality of the light receivers 150. The light emitters 130 are spaced apart from each other and located on the first surface area 113, and the light receivers 150 are spaced apart from each other and located on the second surface area 115. The occupied space of the light emitters 130 and the light receivers 150 can be reduced for improving the light receiving ability of the light receivers 150.

In some embodiments of the present invention, the detection device 100 includes a first wall 161 which is located between the first surface area 113 and the second surface area 115. The first wall 161 is across an interface between the first surface area 113 and the second surface area 115, and the first wall 161 is located on the first surface area 113 and the second surface area 115, simultaneously. In addition, the first wall 161 can be a continuous piece of material or not a continuous piece of material. The first wall 161 surrounds the light emitter 130, in which the first wall 161 has an internal wall surface 161a facing the light emitter 130 and having the first reflectance, and the first wall 161 also has an external wall surface 161b facing the light receiver 150 and having a second reflectance. Therefore, the first wall 161 can prevent the detection light of the light emitters 130 from being directly absorbed by the light receivers 150, and thus the crosstalk between the light emitters 130 and the light receivers 150 can be avoided, such that the light receivers 150 have an outstanding light receiving ability.

In some embodiments of the present invention, the detection device 100 has an annular second wall 163 which extends along a periphery of the second surface area 115, and an internal wall surface 163a of the second wall 163 has the second reflectance lower than the first reflectance, such that the second wall 163 improves the light receiving ability of the light receiver 150. In addition, the light receiver 150 is located between the first wall 161 and the second wall 163, and the external wall surface 161b of the first wall 161 faces the light receiver 150 and has the second reflectance. The internal wall surface 163a of the second wall 163 has the second reflectance, and the first wall 161 as well as the second wall 163 can efficiently absorb the unneeded stray light and avoid the crosstalk between the light emitter 130 and the light receiver 150.

In some embodiments of the present invention, the first wall 161 and the second wall 163 is fixed to the substrate 110 by dispensing, in which the first wall 161 and the second wall 163 can be made of polymer or resin, such as thermoplastic and thermoset plastic. The thermoplastic can include polyphthalamide (PPA), acrylonitrile butadiene styrene (ABS), polyetheretherketone (PEEK), or other suitable materials. The thermoset plastic includes epoxy molding compound (EMC), silicone molding compound (SMC), or other suitable materials. In addition, the first wall 161 and the second wall 163 can also include the aforementioned the opaque materials which include a light-absorbing material or a reflective material.

In some embodiments of the present invention, the detection device 100 further includes the optical top cap 120 which includes an optical lens 121 and an annular third wall 127. The optical lens 121 has an outer surface O and an inner surface I, on which the third wall 127 is located. When the optical top cap 120 is fixed to the substrate 110, the third wall 127 is in contact with the first wall 161 to form a space accommodating the light emitters 130. The first wall 161 and the third wall 127 can both have the first reflectance which is greater than the second reflectance, and thus the light emitter 130 can efficiently generate the detection light which is used to human bodies. Specifically, the annular third wall 127 has an internal wall surface 127a and an external wall surface 127b. The internal wall surface 127a of the third wall 127 has a reflectance substantially equal to the first reflectance, and the external wall surface 127b of the third wall 127 has a reflectance substantially equal to the second reflectance. In addition, the optical lens 121 is a transparent structure which includes a light guiding lens or a light refraction lens, and the optical lens 121 can be made of transparent plastic or transparent glass. The outer surface O and the inner surface I can be flat surfaces, convex curved surfaces, or concave curved surfaces, and the present invention is not limited in this respect.

In addition, the detection device 100 further includes an annular fourth wall 129, and the fourth wall 129 which is located on the inner surface I of the optical lens 121 surrounds the third wall 127. While the optical top cap 120 is fixed to the substrate 110, the light receivers 150 are located between the third wall 127 and the fourth wall 129. Moreover, the fourth wall 129 is in contact with the second wall 163 to form a space accommodating the light receivers 150. The second wall 163 and the fourth wall 129 have the second reflectance lower than the first reflectance for efficiently absorbing the stray light and improving the light receiving ability of the light receivers 150. Specifically, an internal wall surface 129a of the fourth wall 129 has a reflectance substantially the same as the second reflectance. The third wall 127 and the fourth wall 129 can be fixed to the optical lens 121 by dispensing, and the third wall 127 and the fourth wall 129 have substantially the same materials as the first wall 161 and the second wall 163. The detailed information regarding the same materials of the first wall 161 and the second wall 163 hereof are not repeated again.

Figure 5:
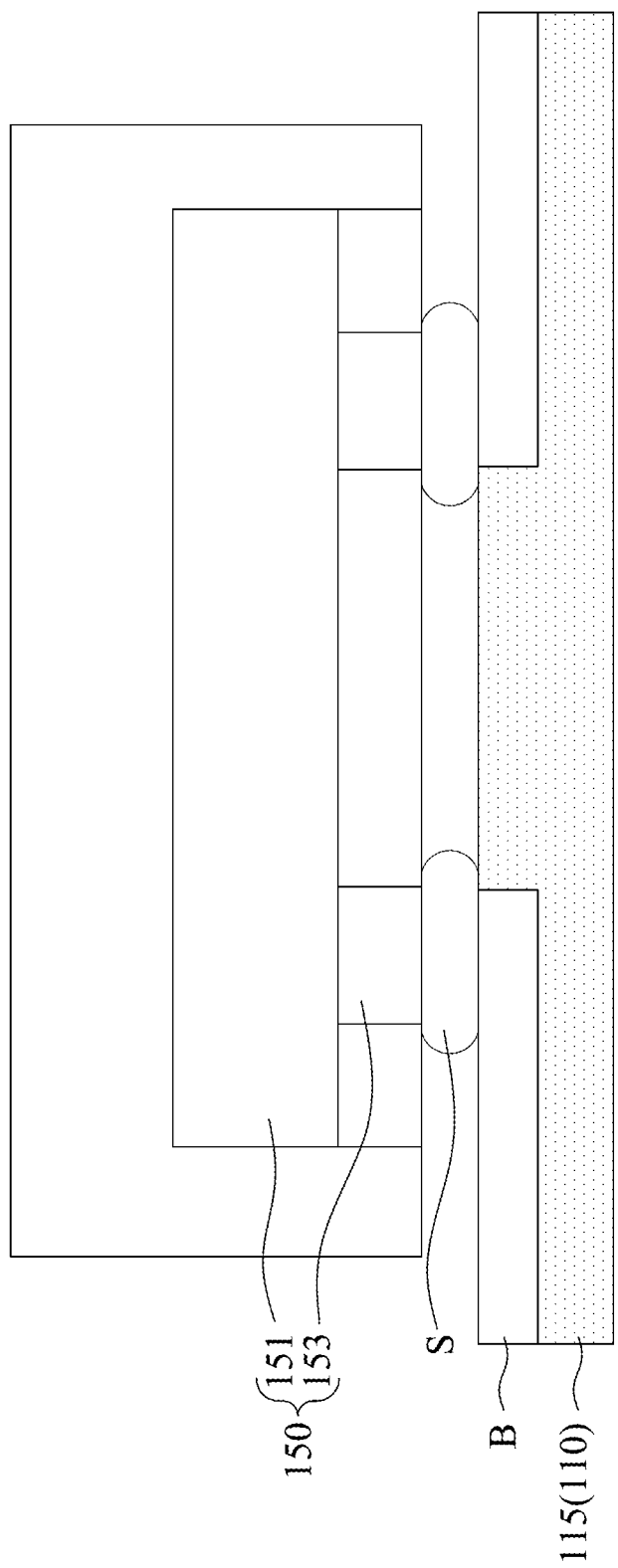
FIG. 5 illustrates a side view of a light receiver in accordance with some embodiments of the present invention.

In some embodiments of the present invention, the light emitters 130 and the light receivers 150 can be disposed on the substrate 110 in a wire bonding package or in a flip chip package. Reference is made to FIG. 5, which illustrates a side view of the light receiver 150, and the light receiver 150 is fixed to the substrate 110 in the flip chip package. The light receiver 150 includes a light sensing area 151 and a conductive end 153, and the substrate 110 includes a bonding pad B. The conductive end 153 is electrically connected to the bonding pad B on the substrate 110, and a solder ball S on the bonding pad B is in contact with the conductive end 153. Therefore, the solder ball S is between the conductive end 153 and the bonding pad B, and the light receiver 150 is electrically connected to the substrate 110. Regarding the flip chip package, the light sensing area 151 of the light receiver 150 faces away from the substrate 110, such that the light sensing area 151 has significantly great area for improving the light receiving ability of the light receiver 150. In some embodiments of the present invention, the light emitter 130 is fixed to the substrate 110 in the flip chip manner shown in FIG. 5.

Figure 6:
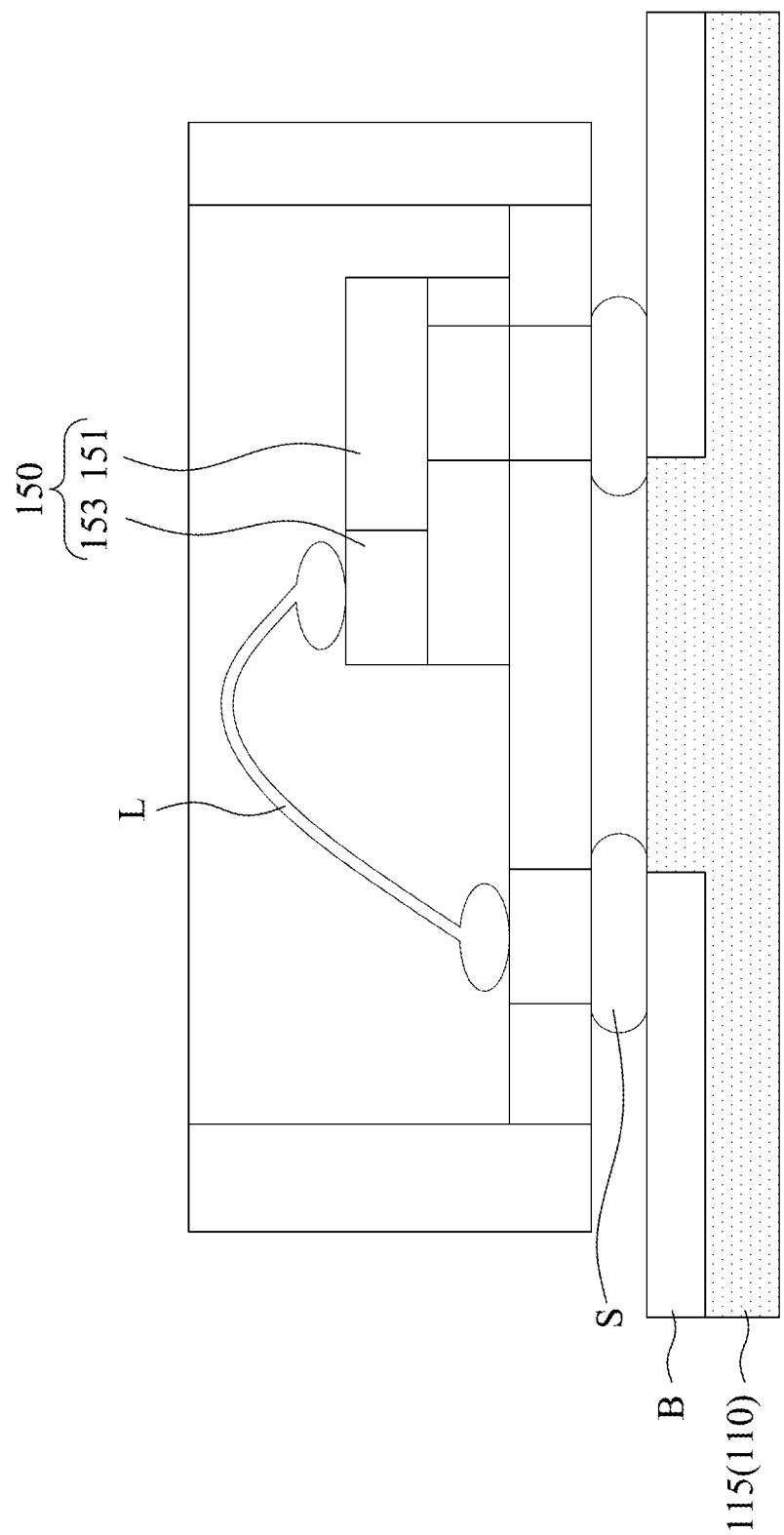
FIG. 6 illustrates a side view of a light receiver in accordance with some embodiments of the present invention.

Reference is made to FIG. 6, which illustrates a side view of the light receiver 150 in accordance with some embodiments of the present invention. The light receiver 150 is fixed to the substrate 110 in the wire bonding package, and a light sensing area 151 and a conductive end 153 of the light receiver 150 faces away from the substrate 110. The conductive end 153 is electrically connected to the bonding pad B and the solder ball S thereon via a metal wire L, so as to enables the light receiver 150 to be electrically connected to the substrate 110. The present invention is not limited in this respect. In some embodiments of the present invention, the light emitter 130 can also be fixed to the substrate 110 in the wire bonding manner shown in FIG. 6.

In embodiments of the present invention, a detection device is provided, and the detection device includes a substrate, a light emitter, and a light receiver. The light emitter with high reflectance is located on an area, and the light receiver with low reflectance is located on another area. Therefore, it is benefit for the light emitter to efficiently generate detection light outward, and stray light around the light receiver is absorbed, so as to prevent the stray light from affecting the light receiver.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A detection device, comprising:
 a substrate comprising a first surface area and a second surface area, wherein the first surface area has a first reflectance greater than a second reflectance of the second surface area;
 a light emitter disposed on the first surface area; and
 a light receiver disposed on the second surface area, wherein the light receiver has a third reflectance which is substantially the same as the second reflectance of the second surface area;
 a first wall disposed between the first surface area and the second surface area, wherein the first wall comprises a surface facing toward the light emitter and having the first reflectance, and wherein the first wall comprises another surface facing toward the light receiver and having the second reflectance.

2. The detection device of claim 1, wherein the light receiver has a color the same as a color of the second surface area.

3. The detection device of claim 1, wherein the second surface area surrounds a periphery of the first surface area.

4. The detection device of claim 3, wherein the first surface area is circular, and the second surface area is annular.

5. The detection device of claim 1 comprising a second wall extending along a periphery of the second surface area.

6. The detection device of claim 5, further comprising an optical top cap which has an optical lens and a third wall, wherein the optical lens has an outer surface and an inner surface, on which the third wall is disposed, and wherein the third wall is in contact with the first wall to form a space accommodating the light receiver.

7. The detection device of claim 6, further comprising a fourth wall disposed on the inner surface, wherein the fourth wall is in contact with the second wall to form a space accommodating the light receiver.

8. The detection device of claim 1, wherein the first reflectance is greater than or equal to 90%, and wherein the second reflectance is smaller than or equal to 10%.

9. The detection device of claim 1, wherein the light emitter is electrically connected to the substrate in a flip chip package or in a wire bonding package.

10. The detection device of claim 1, wherein the light receiver is electrically connected to the substrate in a flip chip package or in a wire bonding package.

* * * * *